US00PP32795P2

(12) United States Plant Patent
Kerley et al.

(10) Patent No.: US PP32,795 P2
(45) Date of Patent: Feb. 2, 2021

(54) ***LAVANDULA* PLANT NAMED 'KERBEEPINK'**

(50) Latin Name: *Lavandula angustifolia*
Varietal Denomination: KERBEEPINK

(71) Applicants: Timothy Edward Kerley, Cambridge (GB); Sarah Elisabeth Kerley, Cambridge (GB); David William Kerley, Cambridge (GB); Priscilla Grace Kerley, Cambridge (GB)

(72) Inventors: Timothy Edward Kerley, Cambridge (GB); Sarah Elisabeth Kerley, Cambridge (GB); David William Kerley, Cambridge (GB); Priscilla Grace Kerley, Cambridge (GB)

( * ) Notice: Subject to any disclaimer, the term of this patent is extended or adjusted under 35 U.S.C. 154(b) by 0 days.

(21) Appl. No.: 16/602,896

(22) Filed: Dec. 19, 2019

(51) Int. Cl.
*A01H 5/02* (2018.01)
*A01H 6/50* (2018.01)

(52) U.S. Cl.
USPC ..... Plt./445

(58) Field of Classification Search
USPC ..... Plt./445, 226
CPC ... A01H 5/02; A01H 5/00; A01H 5/12; A01H 6/50; A01H 6/502
See application file for complete search history.

(56) References Cited

PUBLICATIONS

Downderry Nursery where Lavender comes to life, retrieved on Jun. 24, 2020, retrieved from the Internet at https://downderry-nursery.co.uk/parts-of-a-lavender/, 2 pp. (Year: 2020).*
Issuu Hishtil Catalog 2019-2020 retrieved on Jun. 23, 2020, retrieved from the Internet at https://issuu.com/hishtil4/docs/hishtil_catalog_2019-2020_english__, cover page, 28,103. (Year: 2018).*
Kerley & Co Lavender BEEZEE Pink, retrieved on Jun. 23, 2020, retrieved from the Internet at https://www.kerley.co.uk/variety/pink-5/, one page (Year: 2020).*

* cited by examiner

*Primary Examiner* — June Hwu
(74) *Attorney, Agent, or Firm* — Cassandra Bright

(57) ABSTRACT

A new and distinct cultivar of *Lavandula angustifolia* plant named 'KERBEEPINK' is disclosed, characterized, a compact, bushy plant, which is free flowering, with short peduncles. Flowers are light pink. The new variety is a *Lavandula angustifolia*, suitable for outdoor landscape and container use.

4 Drawing Sheets

Latin name of the genus and species: *Lavandula angustifolia*.
Variety denomination: 'KERBEEPINK'.

BACKGROUND OF THE INVENTION

The new cultivar is the product of a planned breeding program under the direction of the inventors, David Kerley, Priscilla Kerley, Sarah Kerley, and Timothy Kerley, all citizens of the United Kingdom. The objective of the breeding program was to produce new *Lavandula angustifolia* cultivars for commercial ornamental purposes. During the Summer of 2013, the inventors performed an open-pollination of several proprietary, unnamed, unpatented *Lavandula angustifolia* seedlings. Seed was bulk collected and sown. This resulted in the selection of the new variety 'Kerbeepink' in July 2014. The breeding program and selection all took place at a commercial nursery in Cambridge, the United Kingdom.

Asexual reproduction of the new cultivar 'KERBEEPINK' was first performed in Cambridge, UK in August 2014 by terminal vegetative cuttings and has shown that the unique features of this cultivar are stable and reproduced true to type in successive generations.

SUMMARY OF THE INVENTION

The cultivar 'KERBEEPINK' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERBEEPINK' These characteristics in combination distinguish 'KERBEEPINK' as a new and distinct *Lavandula* cultivar:

1. Compact, bushy plants.
2. Short peduncles.
3. Free flowering.
4. Light pink flowers.

PARENTAL COMPARISON

Exact parents cannot be identified for comparison. In general, the new variety is more compact and floriferous than the varieties used in the mass pollination.

COMMERCIAL COMPARISON

Plants of the new cultivar 'KERBEEPINK' are similar to plants of the unpatented variety *Lavandula angustifolia* 'Rosea' in most horticultural characteristics, however, plants of the new cultivar 'KERBEEPINK' differ in the following:

1. The new variety is a shorter plant than this comparator.
2. Flower spikes of this comparator are much more spaced out than flower spikes of the new variety.

Plants of the new cultivar 'KERBEEPINK' are also similar to plants of the unpatented variety *Lavandula angustifolia* 'Little Lottie' in most horticultural characteristics, however, plants of the new cultivar 'KERBEEPINK' differ in the following:

1. The new variety has a more upright habit than this comparator.
2. The new variety is a taller plant than this comparator.

BRIEF DESCRIPTION OF THE PHOTOGRAPHS

The accompanying photograph in FIG. 1 illustrates in full color a typical plant of 'KERBEEPINK' grown outdoors in Cambridge, UK. The plant is approximately 1 year old shown in an approximately 10 inch pot.

Figure 1:
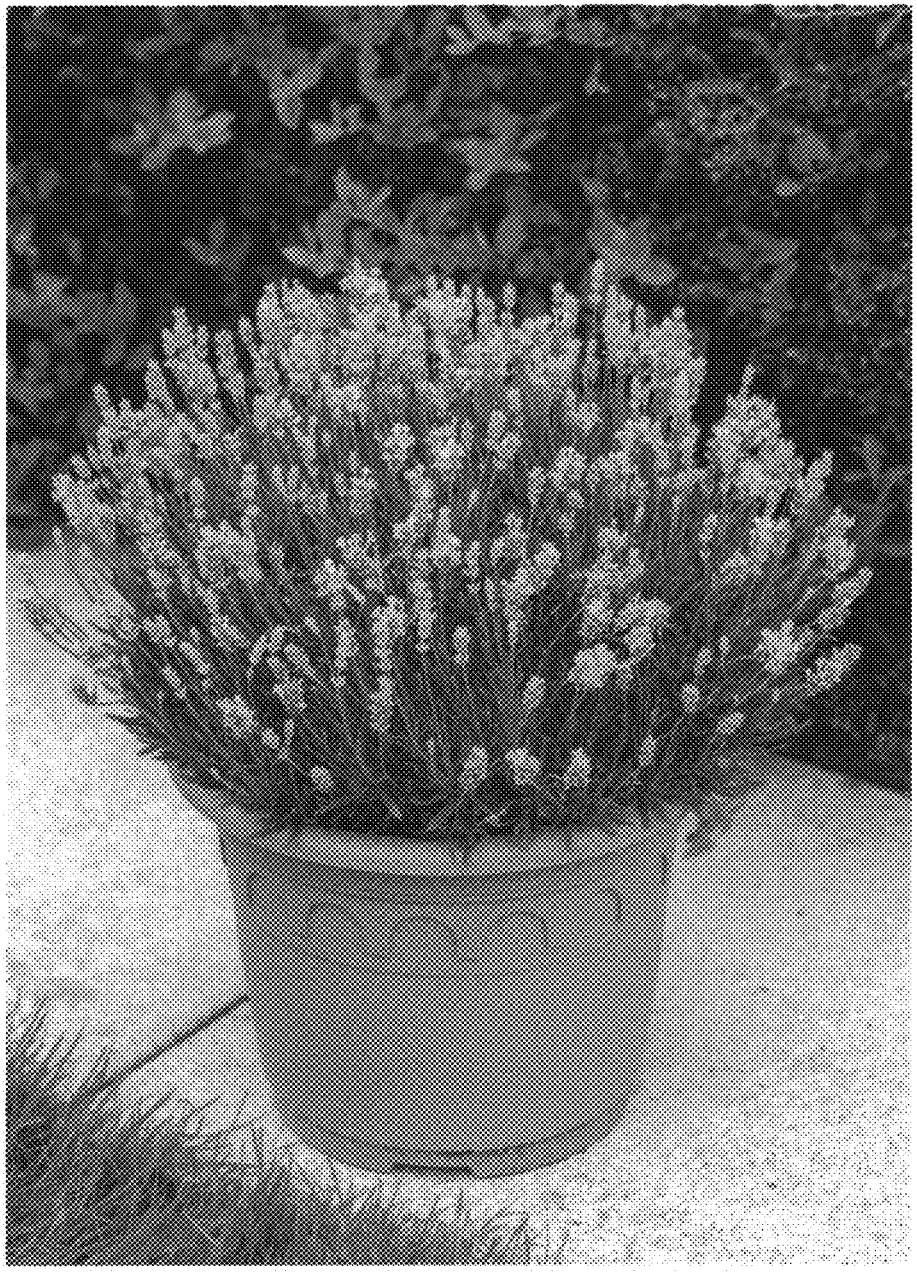
Figure 2:
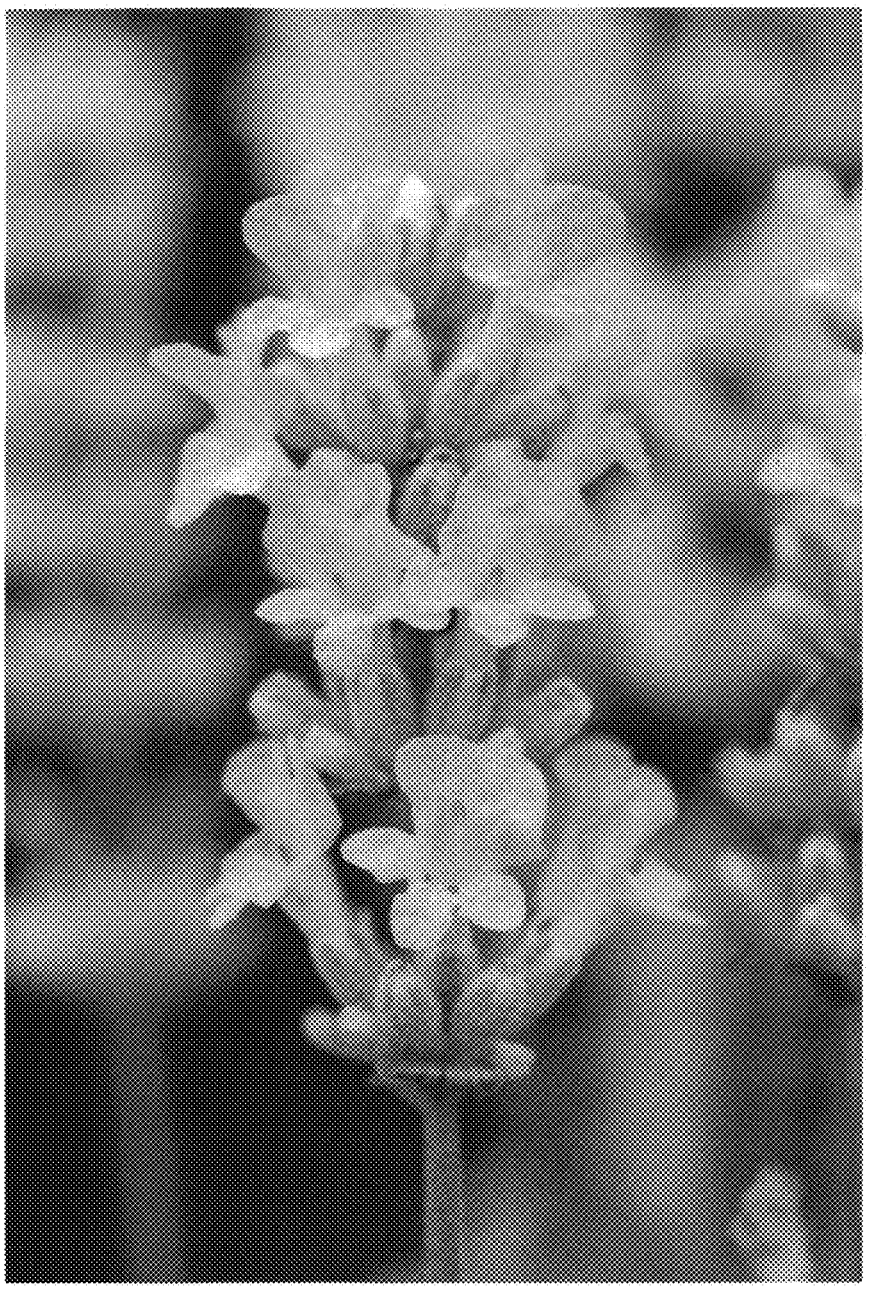
FIG. 2 illustrates a close up view of a typical inflorescence.
Figure 3:
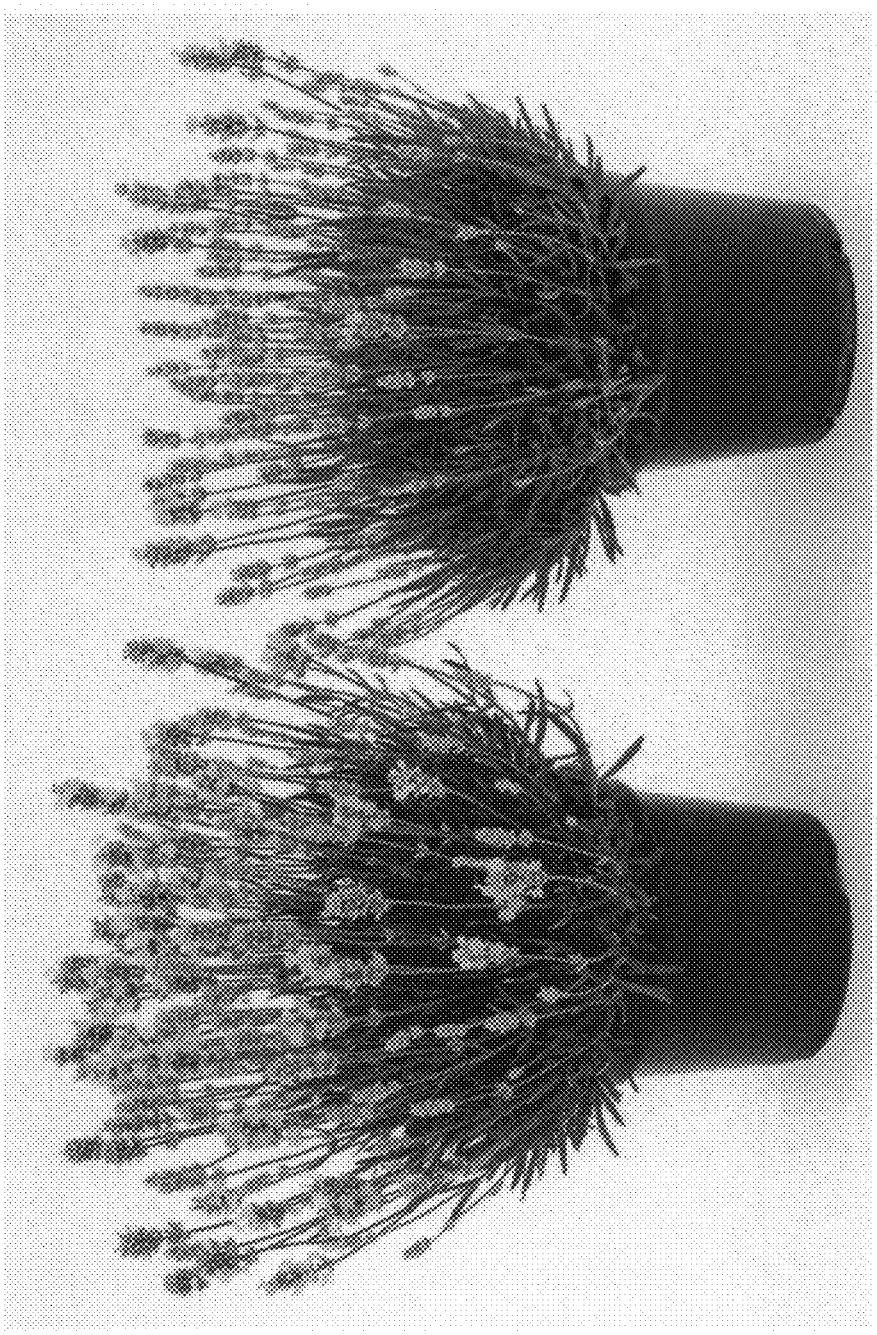
FIG. 3 illustrates a comparison with the well-known commercial variety 'Little Lottie'. 'KERBEEPINK' is the plant on the left side of the photo, 'Little Lottie' is on the right.
Figure 4:
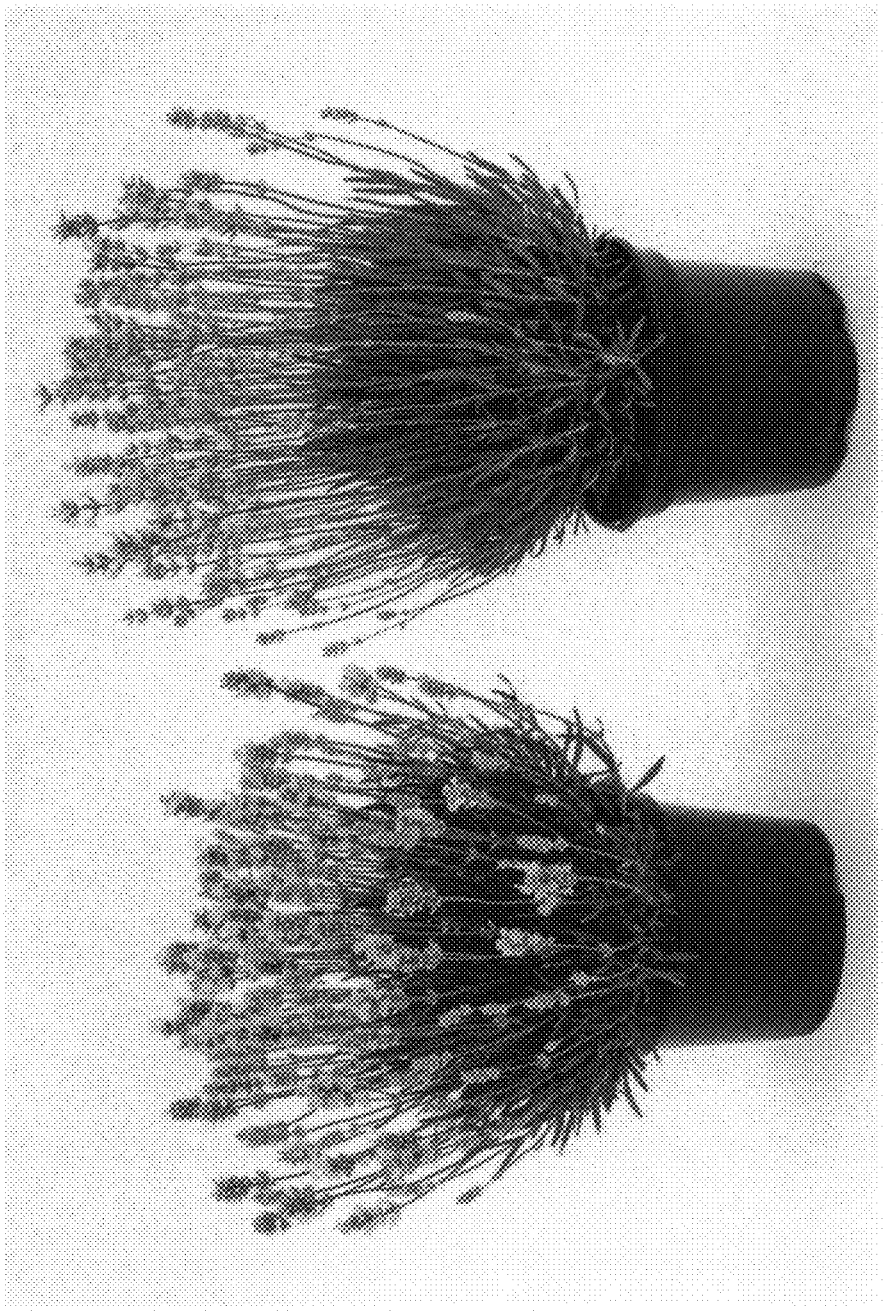
FIG. 4 illustrates a comparison with the commercial variety 'Rosea'. 'KERBEEPINK' is the plant on the left side of the photo, 'Rosea' is on the right.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'KERBEEPINK' plants grown outdoors in Cambridge, UK. The growing temperature ranged from approximately 0 to 10° C. at night to 10 to 20° C. during the day. Measurements and numerical values represent averages of typical flowering types. No chemical or photoperiodic treatments were given.

Botanical classification: *Lavandula angustifolia* 'KERBEEPINK.'

Age of the plant described: Approximately 17 weeks, in a 2 liter pot.

PROPAGATION

Time to rooting: About 21 days at approximately 20° C.

Root description: Fine, well branched, becoming woody with age.

PLANT

Growth habit: Upright. Dense at full flowering.

Height: 14 cm to top of plant plane; 27 cm to top of flowers.

Plant spread: 22 cm.

Branching characteristics: Moderate branching.

Diameter of lateral branches: Approximately 0.2 cm.

Texture of lateral branches: Pubescent.

Internode length: Approximately 1.3 cm.

Strength of stem: Strong.

Color of lateral branches: Near RHS Yellow-Green 146D.

Number of leaves per lateral branch: 13.

FOLIAGE

Leaf:

*Arrangement.*—Opposite pairs — alternate directions.

*Average length.*—3.5 cm.

*Average width.*—0.5 cm.

*Shape of blade.*—Oblanceolate.

*Apex.*—Acute.

*Base.*—Cuneate.

*Attachment.*—Sessile.

*Margin.*—Entire.

*Texture of top surface.*—Pubescent.

*Texture of bottom surface.*—Pubescent.

*Color.*—Young foliage, upper side: RHS Yellow-Green 146A. Young foliage, under side: RHS Yellow-Green 146B. Mature foliage upper side: RHS Yellow-Green 147A. Mature foliage under side: RHS Yellow-Green 147B.

*Venation.*—Type: One prominent mid-vein, with a fine network of smaller veins. Venation color upper side: RHS Yellow-Green 146B. Venation color under side: RHS Yellow-Green 146A.

Petiole: Not present.

FLOWER

Bloom period: Naturally blooming June to July.

Inflorescence:

*Form.*—Small single flower in verticillasters arranged in spikes. Flowers have bracts. Corolla has 2 upper lips and 3 lower lips.

Flower spikes:

*Height.*—3.8 cm.

*Diameter.*—1.8 cm.

*Shape.*—Cylindrical.

*Flowers per spike.*—Average range of 30 to 36 individual flowers per spike, arranged in 5 to 6 whorls, each whorl typically having 6 flowers. Short distance between whorls, about 5 mm.

Flower bud:

*Height.*—0.6 cm.

*Width.*—0.3 cm.

*Color.*—Base RHS Greyed-Green 193A at base, Red-Purple 69D towards tip.

Individual flower:

*Corolla-length of upper lobes* (2).—0.5 cm.

*Corolla-length of lower lobes* (3).—0.4 cm.

*Corolla-width of upper lobes.*—0.6 cm.

*Corolla-width of lower lobes.*—0.3 cm.

*Corolla tube length.*—About 0.3 cm.

*Shape of upper lobes.*—2 conjoined lobes.

*Shape of lower lobes.*—3 smaller lobes, fused about half-length.

*Apex of upper lobes.*—Blunt and rounded.

*Apex of lower lobes.*—Mucronate, slightly undulating.

*Texture of corolla.*—Upper surface: Savoyed and glabrous.

*Texture of corolla.*—Lower surface: Savoyed and pubescent on veins.

*Color when opening.*—Upper surface: RHS Purple 76B.

*Color when opening.*—Lower surface: RHS Purple 76C.

*Color when fully open*.—RHS Purple-Violet N80D, with a hint of N80B towards center.
*Corolla tube color*.—Exterior RHS Purple 76C. Interior RHS Purple 76D.
*Calyx shape*.—Tube.
*Calyx width*.—0.3 cm.
*Sepal length*.—0.5 cm.
*Sepal texture*.—Very hirsute. Hairs RHS Greyed-Green 196B.
*Sepal color*.—Flower open: RHS Greyed-Green 195B.
*Sepal color*.—Fully open: RHS Yellow-Green 148C.

Inflorescence bracts:
*Bract width*.—0.4 cm.
*Bract height*.—0.6 cm.
*Bract color*.—Near RHS Greyed-Orange 165A.

Peduncle:
*Peduncle length*.—10.9 cm.
*Peduncle diameter*.—0.2 cm.
*Aspect*.—Upright.
*Color*.—RHS Yellow-Green 147B.
*Branching*.—Lateral branching above foliage not observed.

Other: Infertile bracts not observed.

REPRODUCTIVE ORGANS

Filament length: 0.3 cm.
Anther length: 0.2 cm.
Anther color: RHS Greyed-Orange 166A.
Pollen color: RHS Greyed-Orange 167A.
Pollen amount: Sparse.
Pistil length: 0.8 cm.
Style length: 0.5 cm.
Style color: RHS Greyed-Green 195C.
Stigma color: RHS Greyed-Green 195A, with a hint of Purple-Violet N80C at tip.

OTHER CHARACTERISTICS

Fragrance: Strong lavender scent, both flowers and foliage.
Disease resistance: Neither resistance nor susceptibility to diseases or pests has been observed in this variety.
Drought tolerance and cold tolerance: Hardy perennial. Tolerates high temperature to at least 32° C. Tolerates low temperatures to −12° C. While specific drought tolerance has not been observed, once plants are established very little water is necessary to maintain plants.
Fruit/seed production: Fruit and seed production not observed.

What is claimed is:

1. A new and distinct cultivar of *Lavandula* plant named 'KERBEEPINK' as herein illustrated and described.

* * * * *